(12) United States Patent
Naya

(10) Patent No.: US 7,288,419 B2
(45) Date of Patent: Oct. 30, 2007

(54) MICROSTRUCTURE FOR USE IN RAMAN SPECTROMETRY AND PRODUCTION PROCESS FOR THE MICROSTRUCTURE

(75) Inventor: Masayuki Naya, Kanagawa-ken (JP)

(73) Assignee: FujiFilm Corporation, Tokyo (JP)

( * ) Notice: Subject to any disclaimer, the term of this patent is extended or adjusted under 35 U.S.C. 154(b) by 308 days.

(21) Appl. No.: 11/008,180

(22) Filed: Dec. 10, 2004

(65) Prior Publication Data

US 2005/0105085 A1    May 19, 2005

(30) Foreign Application Priority Data

Oct. 12, 2003  (JP)  ............... 2003-411790

(51) Int. Cl.
*H01L 21/76* (2006.01)
*G01J 3/44* (2006.01)

(52) U.S. Cl. .......................... 438/20; 356/301

(58) Field of Classification Search ............... 356/301; 257/659, 680; 438/20
See application file for complete search history.

(56) References Cited

U.S. PATENT DOCUMENTS 6,838,297 B2 * 1/2005 Iwasaki et al. ............. 438/20
2004/0183176 A1 * 9/2004 Naya et al. ................. 257/680

FOREIGN PATENT DOCUMENTS

EP        0 984 269 A1    3/2000

OTHER PUBLICATIONS

Vo-Dinh T: "Surface-enhanced Raman spectroscopy using metallic nanostructures", TRAC, Trends in Analytical Chemistry, Analytical Chemistry. Cambridge, GB, vol. 17, No. 8-9, Aug. 9, 1998, pp. 557-582.

Yao J L et al: "A Complementary Study of Surface-Enhanced Raman Scattering and Metal Nanorod Arrays", Pure & Applied Chemistry, Pergamon Press, Oxford, GB, vol. 72, No. 1, 2000, pp. 221-228, XP001205200.

Felidj N et al: "Optimized surface-enhanced Raman scattering on gold nanoparticle arrays", Applied Physics Letters, American Institute of Physics. New York, US, vol. 82, No. 18, May 5, 2003, pp. 3095-6951.

"A Complementary Study of Surface-Enhanced Raman Scattering and Metal Nanorod Arrays", J. L. Yao et al., Pure Appl. Chem., vol. 72, No. 1, pp. 221-228 (2000).

* cited by examiner

*Primary Examiner*—Gregory J. Toatley, Jr.
*Assistant Examiner*—Abdullahi Nur
(74) *Attorney, Agent, or Firm*—Sughrue Mion Pllc.

(57) ABSTRACT

In a microstructure: minute pores are formed at a surface of a substrate in such a manner that the minute pores are dispersedly distributed over the surface, and the gaps between the minute pores are 1 micrometer or smaller; minute metal particles are arranged at the minute pores and have such sizes that the minute metal particles can cause localized plasmon resonance; the minute metal particles have head portions protruding from the surface; and the diameters of the head portions are greater than the diameters of the minute pores. In Raman spectrometry, a specimen material is absorbed by the surface from which the head portions protrude, light is applied to the surface, and a spectrum of scattered light is obtained.

14 Claims, 3 Drawing Sheets

US 7,288,419 B2

MICROSTRUCTURE FOR USE IN RAMAN SPECTROMETRY AND PRODUCTION PROCESS FOR THE MICROSTRUCTURE

BACKGROUND OF THE INVENTION

1. Field of the Invention

The present invention relates to a microstructure suitable for use in Raman spectrometry. The present invention also relates to a process for producing a microstructure suitable for use in Raman spectrometry. The present invention further relates to a process for performing Raman spectrometry and a Raman spectrometric system using the above microstructure.

2. Description of the Related Art

In Raman spectrometry, a material is irradiated with monochromatic excitation light, scattered light (called Raman scattered light) having wavelengths different from the wavelength of the excitation light is obtained, and a spectrum of the Raman scattered light (called Raman spectrum) is analyzed. The Raman scattered light has a very low intensity, and therefore detection of the Raman scattered light is generally not easy. However, it is reported that the intensity of the Raman scattered light is increased by a factor of $10^4$ to $10^6$ when the specimen (material to be analyzed) is absorbed by a metal surface before the irradiation. In particular, it is known that the intensity of the Raman scattered light is greatly increased when nanometer-size metal particles are dispersedly distributed over the surface by which the material to be analyzed is to be absorbed, as disclosed in "A complementary study of surface-enhanced Raman scattering and metal nanorod arrays", J. L. Yao et al., Pure Appl. Chem., Vol. 72, No. 1, pp. 221-228 (2000). It is considered that the localized plasmon resonance increases the intensity of the Raman scattered light. That is, It is considered that free electrons in the nanometer-size metal particles vibrate in resonance with the electric field of the light, the vibration of the free electrons produces strong electric fields in the vicinities of the nanometer-size metal particles, and the strong electric fields increase the intensity of the Raman scattered light.

According to the process disclosed in the Yao reference, a device having a structure in which nanometer-size metal particles are dispersedly distributed is produced by forming an alumina layer by anodic oxidation of aluminum, and filling minute pores which are spontaneously formed at the surface of the alumina layer during the anodic oxidation, with metal. Specifically, after the minute pores are filled with the metal, the upper portion of the alumina layer is removed by etching so that upper portions of the minute metal particles protrude. Thus, the strong electric fields generated around the tips of the head portions of the minute metal particles increase the intensity of the Raman scattered light.

In the above structure, when the minute metal particles protrude higher, the intensity of the Raman scattered light is more increased. However, the time for which the alumina layer is etched exceeds a predetermined time, the head portions of the minute metal particles are broken down by the etching. Therefore, it is not easy to make the head portions of the minute metal particles protrude sufficiently high.

SUMMARY OF THE INVENTION

An object of the present invention is to provide a microstructure having a function of increasing the intensity of Raman scattered light, exhibiting high performance, having high quality, being easy to manufacture, and enabling stable supply.

Another object of the present invention is to provide a process for producing a microstructure having a function of increasing the intensity of Raman scattered light, exhibiting high performance, having high quality, being easy to manufacture, and enabling stable supply.

Still another object of the present invention is to provide a process for performing Raman spectrometry by using a microstructure which has a function of increasing the intensity of Raman scattered light, exhibits high performance, has high quality, is easy to manufacture, and enables stable supply.

A further object of the present invention is to provide a Raman spectrometric system for performing Raman spectrometry by using a microstructure which has a function of increasing the intensity of Raman scattered light, exhibits high performance, has high quality, is easy to manufacture, and enables stable supply.

(1) According to the first aspect of the present invention, there is provided a microstructure comprising: a substrate having a surface at which a plurality of minute pores are formed; and a plurality of minute metal particles being arranged at the plurality of minute pores and having such sizes that the plurality of minute metal particles can cause localized plasmon resonance. In the microstructure, the plurality of minute pores are dispersedly distributed over the surface in such a manner that gaps between adjacent ones of the plurality of minute pores are 1 micrometer or smaller, the plurality of minute metal particles have head portions protruding from the surface, and the head portions have first diameters greater than second diameters which the plurality of minute pores have.

That is, in the microstructure according to the first aspect of the present invention, the plurality of minute metal particles having such sizes that the plurality of minute metal particles can excite localized plasmon resonance are arranged at the plurality of minute pores which are distributed with high density, and the diameters of the head portions of the plurality of minute metal particles (which are referred to as the first diameters) are greater than the diameters of the plurality of minute pores (which are referred to as the second diameters).

It is known that the electric fields in the spaces between the plurality of minute metal particles are stronger than the electric fields in the other spaces. Therefore, when the gaps between the plurality of minute metal particles are reduced by making the diameters of the head portions of the plurality of minute metal particles greater than the diameters of the plurality of minute pores, the effect of increasing the intensity of the Raman scattered light can be enhanced.

Thus, when a specimen material is absorbed by the surface of the microstructure on which the minute metal particles are arranged as above, and light is applied to the surface, the intensity of the Raman scattered light is increased by a great factor, and therefore the Raman scattered light can be detected with high accuracy.

Preferably, the microstructure according to the first aspect of the present invention may have one or any possible combination of the following additional features (i) to (vi).

(i) The gaps between the head portions of adjacent ones of the plurality of minute metal particles are 10 nm or smaller.

(ii) The substrate has as a surface layer an alumina layer which is formed by anodic oxidation of a material containing aluminum as a main component, and the plurality of minute pores are formed during the anodic oxidation.

The minute pores which are spontaneously formed during the anodic oxidation of aluminum or the like are arranged with high regularity. Therefore, when the plurality of minute pores in the microstructure according to the first aspect of the present invention has the feature (ii), the plurality of minute metal particles are uniformly arranged, and thus the arrangement of the entire microstructure becomes uniform. However, it is possible to form the plurality of minute pores by any other method.

(iii) The first diameters are 200 nm or smaller.
(iv) The plurality of minute pores have depths of 100 nm or smaller.
(v) The second diameters have a variance of 15% or smaller.
(vi) The plurality of minute metal particles are made of one of gold, silver, aluminum, and copper.

(2) According to the second aspect of the present invention, there is provided a process for producing a microstructure in which a plurality of minute metal particles having such sizes that the plurality of minute metal particles can cause localized plasmon resonance are dispersedly distributed over a surface. The process comprises the steps of: (a) forming a plurality of minute pores in a surface layer of a substrate in such a manner that the plurality of minute pores are dispersedly distributed, and the gaps between adjacent ones of the plurality of minute pores are 1 micrometer or smaller; (b) filling the plurality of minute pores with metal by plating so as to form base portions of the plurality of minute metal particles; and (c) continuing the plating until head portions are formed on the base portions of the plurality of minute metal particles, where the head portions protrude from the surface layer and have first diameters greater than second diameters which the plurality of minute pores have.

That is, the microstructure according to the first aspect of the present invention can be produced by the process according to the second aspect of the present invention.

In the process according to the second aspect of the present invention, the minute pores are filled with metal and the minute metal particles are formed by excessively performing plating so that the diameters of the head portions of the minute metal particles become greater than the diameters of the minute pores. In this process, etching is unnecessary for making the head portions of the minute metal particles protrude, and the minute metal particles do not break down during the formation of the minute metal particles. In addition, since the head portions of the minute metal particles are formed so that the diameters of the head portions of the minute metal particles are greater than the diameters of the minute pores, it is possible to make the gaps between the head portions of adjacent ones of the minute metal particles very small and enhance the effect of increasing the intensity of the Raman scattered light even in the case where the minute pores cannot be arranged so closely due to a limit in the technique of forming the minute pores.

Preferably, the process according to the second aspect of the present invention may have one or a combination of the following additional features (vii) and (viii).

(vii) The substrate is made of a material containing aluminum as a main component, and the plurality of minute pores are formed in the surface layer by anodic oxidation of the substrate.

Although the plurality of minute pores can be formed by using other fine fabrication techniques such as electron beam exposure, nanoimprinting, and near-field light lithography, the regular arrangement of the plurality of minute pores can be more easily realized when anodic oxidation of a material containing aluminum as a main component is used.

(viii) The plating is continued until the gaps between the head portions of adjacent ones of the plurality of minute metal particles become 10 nm or smaller.

(3) According to the third aspect of the present invention, there is provided a process for performing Raman spectrometry, comprising the steps of: (a) making a specimen material absorbed by a first surface of a microstructure; (b) applying light to the first surface of the microstructure; and (c) obtaining a spectrum of scattered light generated by scattering of the light at the first surface of the microstructure. In the process, the microstructure includes: a substrate having a second surface at which a plurality of minute pores are formed; and a plurality of minute metal particles being arranged at the plurality of minute pores and having such sizes that the plurality of minute metal particles can cause localized plasmon resonance; and the plurality of minute pores are dispersedly distributed over the second surface in such a manner that the gaps between adjacent ones of the plurality of minute pores are 1 micrometer or smaller, the plurality of minute metal particles have head portions protruding from the second surface, and the head portions have first diameters greater than second diameters which the plurality of minute pores have. The head portions and the second surface constitute the first surface.

That is, in the process for performing Raman spectrometry according to the third aspect of the present invention, the microstructure according to the first aspect of the present invention is used as a device for absorbing the specimen material. Since the intensity of the Raman scattered light is sufficiently increased by the use of the microstructure according to the first aspect of the present invention, the Raman scattered light can be detected with high accuracy.

Preferably, in the process according to the third aspect of the present invention, the gaps between the head portions of adjacent ones of the plurality of minute metal particles are 10 nm or smaller.

(4) According to the fourth aspect of the present invention, there is provided a Raman spectrometric system comprising: a microstructure having a first surface; a light application unit which applies light to the first surface of the microstructure; and a spectroscopic unit which obtains a spectrum of scattered light generated by scattering of the light at the first surface of the microstructure. In the Raman spectrometric system according to the fourth aspect of the present invention, the microstructure includes: a substrate having a second surface at which a plurality of minute pores are formed; and a plurality of minute metal particles being arranged at the plurality of minute pores and having such sizes that the plurality of minute metal particles can cause localized plasmon resonance. In the microstructure, the plurality of minute pores are dispersedly distributed over the second surface in such a manner that the gaps between adjacent ones of the plurality of minute pores are 1 micrometer or smaller, the plurality of minute metal particles have head portions protruding from the second surface, and the head portions have first diameters greater than second diameters which the plurality of minute pores have. The head portions and the second surface constitute the first surface.

That is, the Raman spectrometric system according to the fourth aspect of the present invention comprises the microstructure according to the first aspect of the present invention as a device for absorbing the specimen material. Therefore, the Raman spectrometric system according to the fourth aspect of the present invention can detect the Raman scattered light with high accuracy.

Preferably, in the Raman spectrometric system according to the fourth aspect of the present invention, the gaps between the head portions of adjacent ones of the plurality of minute metal particles are 10 nm or smaller.

DESCRIPTION OF PREFERRED EMBODIMENTS

An embodiment of the present invention is explained in detail below with reference to the drawings.

Microstructure

First, a process for producing a microstructure according to the present embodiment is explained with reference to FIGS. 1A to 1C, which are schematic cross-sectional views of structures in representative stages of a process for producing a microstructure according to the embodiment of the present invention. Although the microstructure according to the present invention can be formed by using various processes, a process using an aluminum substrate is explained below.

Figure 1A:
FIGS. 1A to 1C are schematic cross-sectional views of structures in representative stages of a process for producing a microstructure according to an embodiment of the present invention.

FIG. 1A is a schematic cross-sectional view of a substrate 1 before the process for producing the microstructure is started. In this example, the substrate 1 is made of only an aluminum layer 4. Alternatively, the substrate 1 may be constituted by a support made of a material other than aluminum and a layer of aluminum or an aluminum alloy formed on the support. That is, only the surface layer of the substrate 1 is required to be made of a material containing aluminum as a main component, and the other portions of the substrate 1 is not specifically limited.

In the first step, a surface of the substrate 1 is anodically oxidized by using an anodic oxidation system. In order to anodically oxidize the surface of the substrate 1, first, the substrate 1 is fixed to a holder, and placed in an electrolyte solution in a reaction vessel together with a counter electrode. The electrolyte solution is an acid electrolyte solution containing oxalic acid, phosphoric acid, sulfuric acid, chromic acid, or the like. Alternatively, the electrolyte solution may be a mixture of two or more acid solutions.

Next, a voltage is applied between the substrate 1 and the counter electrode. At this time, the substrate 1 is connected to a positive output of a power supply, and the counter electrode is connected to a negative output of the power supply. When the voltage is applied, first, an oxide film is formed on a surface of the substrate 1, and minute pores are formed at the surface of the oxide film due to acid dissolution. When the anodic oxidation progresses, portions of the minute pores preferentially grow, and arranged at nearly equal spaces. Since stronger electric fields are applied to the portions at which the minute pores are formed, dissolution of the portions are enhanced, and the minute pores grow in the direction perpendicular to the surface of the substrate 1. On the other hand, the portions of the surface around the minute pores remain undissolved. The highly regular arrangement of the spontaneously formed minute pores is one of the characteristic features of the alumina obtained by anodic oxidation.

Figure 1B:
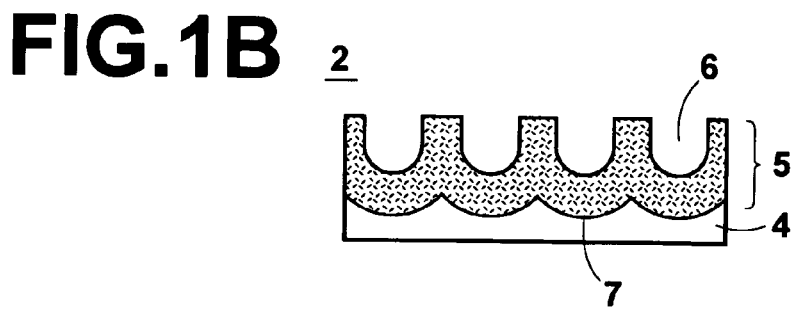
Figure 1C:
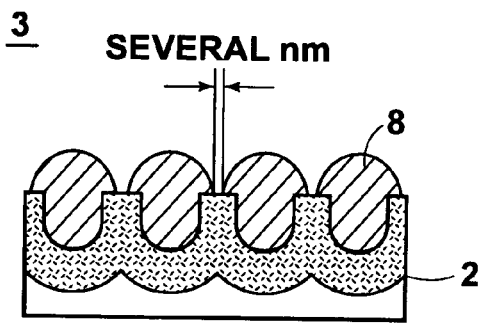

FIG. 1B is a schematic cross-sectional view of the substrate 2 in which an alumina layer 5 having a plurality of minute pores 6 in its near-surface portion is formed. The minute pores 6 are regularly formed over the almost entire surface of the substrate. The diameters and depths of and the gaps between the minute pores 6 vary with the conditions of the anodic oxidation (e.g., the concentration and temperature of the electrolyte solution used in the anodic oxidation, the manner and time of application of the voltage, the voltage value, and the like). Although, normally, the gaps between (pitch of) the minute pores can be accurately controlled within the range of 10 to 500 nm, and the diameters of the minute pores can also be accurately controlled within the range of 5 to 400 nm, the conditions of the anodic oxidation in the present embodiment are set so that the minute pores have diameters of about 200 nm and depths of about 100 nm, and the gaps between (pitch of) the minute pores become about 300 nm.

U.S. Pat. Nos. 6,784,007 and 6,610,463 disclose techniques for more finely controlling the positions of formation and the diameters of the minute pores. When the techniques disclosed in these patent publications are used, it is possible to form minute pores having arbitrary desired diameters and arbitrary depths at arbitrary desired spaces, and limit the variance in the diameters of the minute pores to 15% or smaller.

Next, the minute pores 6 spontaneously formed by the anodic oxidation are filled with gold (Au) by electroplating. In order to perform electroplating, it is necessary to establish conductivity at the bottoms 7 of the minute pores. For example, the conductivity at the bottoms 7 can be established by reducing the thicknesses of the alumina layer 5 at the bottoms of the minute pores. The thicknesses of the alumina layer 5 at the bottoms 7 of the minute pores can be reduced, for example, by controlling the conditions of the anodic oxidation, repeating the anodic oxidation a plurality of times, or removing the alumina layer 5 at the bottoms 7 of the minute pores.

The electroplating is realized by processing the substrate 2 in a plating solution. While the alumina layer 5 per se is nonconductive, the conductivity at the bottoms 7 of the alumina layer 5 is established by the above operation. Therefore, the electric fields in the minute pores 6 are relatively strong, and the metal (gold) is preferentially deposited in the minute pores 6, so that the minute pores 6 are filled with gold.

In the conventional process of producing minute metal particles, normally the plating is completed at the time the minute pores 6 are filled with the metal, i.e., at or before the time the upper surfaces of the metal deposited in the minute pores become even with the upper surface of the substrate 2.

In the process disclosed in the Yao reference, after the minute pores are filled with the metal, the upper portion of the alumina layer is removed by etching so that upper portions of the metal particles protrude. However, in the process for producing the microstructure according to the present invention, the plating is continued even after the upper surfaces of the metal deposited in the minute pores become even with the upper surface of the substrate 2 (i.e., even after the minute pores 6 are completely filled with gold) until the areas around the minute pores 6 are also plated with excessive gold. In other words, only the base portions of the minute gold particles 8 are formed by the filling of the minute pores 6 with gold, and formation of the entire minute gold particles 8 is completed by forming the head portions of the minute gold particles 8 on the base portions. Even after the minute pores 6 are completely filled with gold, gold is preferentially deposited around the minute pores 6 by the influence of the relatively strong electric fields around the minute pores 6. Therefore, when the plating is continued after the minute pores 6 are completely filled with gold, the head portions of the minute gold particles 8 protruding from the surface of the substrate 2 and having the diameters greater than the diameters of the minute pores 6 (e.g., mushroom-shaped head portions as illustrated in FIG. 1C) are formed.

According to the present embodiment, the plating is continued until the gaps between the head portions of adjacent ones of the minute gold particles 8 become 10 nm or smaller. For example, a plating time which makes the gaps between the head portions of adjacent ones of almost all of the minute gold particles 8 10 nm or smaller is experimentally obtained in advance. In the experiment, measurement of gaps between the head portions of adjacent ones of the minute gold particles is repeated during plating by using an electron microscope. In the manufacturing stage, the plating time is managed based on the experimental result. Thus, it is possible to terminate the plating operation at the time the gaps between the head portions of adjacent ones of the minute gold particles 8 become 10 nm or smaller.

The process for producing a microstructure according to the present embodiment described above has the following advantages:

(a) The etching process as disclosed in the Yao reference is unnecessary, and therefore the break down of the minute metal particles during the etching process does not occur.

(b) Since the minute metal particles are formed by plating only, production of the microstructure is relatively easy.

(c) It is possible to obtain a microstructure in which the head portions of minute gold particles are arranged in such a manner that the gaps between the head portions of adjacent ones of minute gold particles are very small. Even when the minute pores are formed by techniques which cannot realize sufficiently small gaps between the minute pores, the gaps between the head portions of adjacent ones of minute gold particles can be reduced to several nanometers by use of the process of according to the present embodiment.

Figure 2:
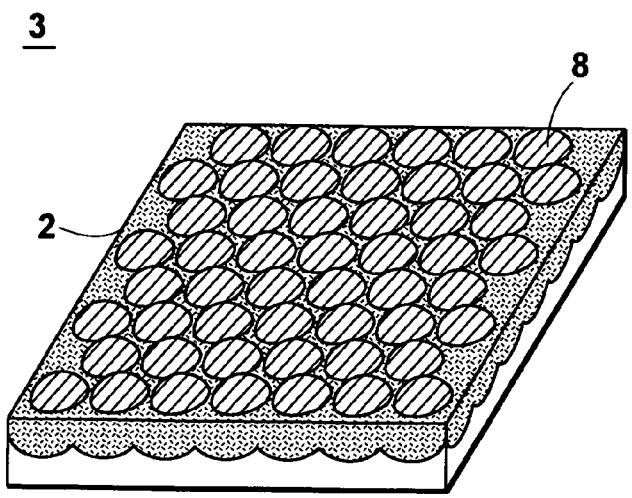
FIG. 2 is a schematic perspective view of the microstructure according to the embodiment.

FIG. 2 is a schematic perspective view of the microstructure according to the present embodiment. As illustrated in FIG. 2, the minute gold particles 8 are arranged with high density over the entire surface of the microstructure 3. The minute pores 6 in the microstructure 3 have diameters of about 200 nm and depths of about 100 nm (i.e., halves of the diameters). The entire surface of the microstructure 3 is uniformly arranged, and the variance in the diameters of the minute pores is 15% or smaller. The diameters of the base portions of the minute gold particles 8 are slightly smaller than the diameters of the minute pores 6, and about 200 nm. The diameters of the head portions of the minute gold particles 8 are greater than the diameters of the minute pores 6, and the gaps between the head portions of adjacent ones of the minute gold particles 8 are several nanometers.

Raman Spectrometric System

Hereinbelow, a Raman spectrometric system using the microstructure 3 illustrated in FIGS. 1C and 2 and a process for performing Raman spectrometry by using the Raman spectrometric system are explained.

Figure 3:
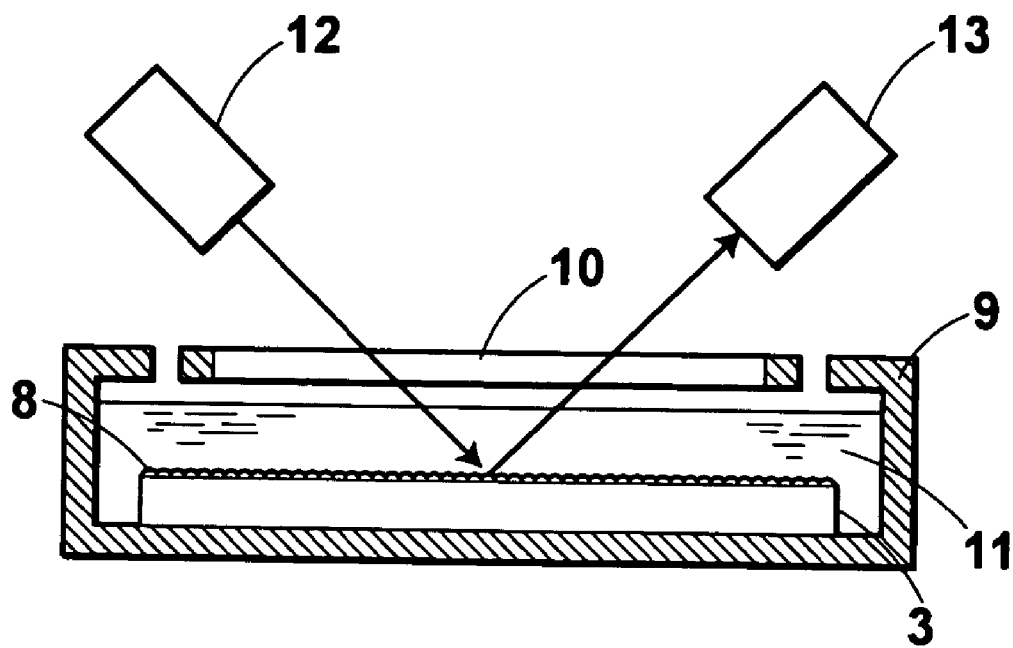
FIG. 3 is a schematic cross-sectional view of a Raman spectrometric system.

FIG. 3 is a schematic cross-sectional view of the Raman spectrometric system according to the present embodiment. As illustrated in FIG. 3, the Raman spectrometric system comprises a vessel 9, the microstructure 3 according to the present embodiment, a laser-light source 12, and a spectrometric detector 13. The vessel 9 has a transparent window 10, and the microstructure 3 is fixed to the inside bottom surface of the vessel 9 in such a manner that the surface from which the head portions of the minute gold particles 8 protrude faces upward. The laser-light source 12 applies laser light to the microstructure 3 in the vessel 9. The spectrometric detector 13 receives scattered light from the surface of the microstructure 3, obtains a spectrum of the scattered light, and detects Raman scattered light included in the scattered light. In addition, the vessel 9 is filled with a liquid specimen 11 which is to be subject to the Raman spectrometry, and at least a component of the liquid specimen 11 is absorbed by the surface of the microstructure 3.

When the laser-light source 12 applies the laser light to the microstructure 3 through the transparent window 10, the laser light is scattered at the surface of the microstructure 3, and the scattered light is received by the spectrometric detector 13. The spectrometric detector 13 detects a spectrum of the received, scattered light, and obtains a Raman spectrum. The obtained Raman spectrum is displayed on a monitor screen (not shown) or outputted to a printer (not shown).

Figure 4:
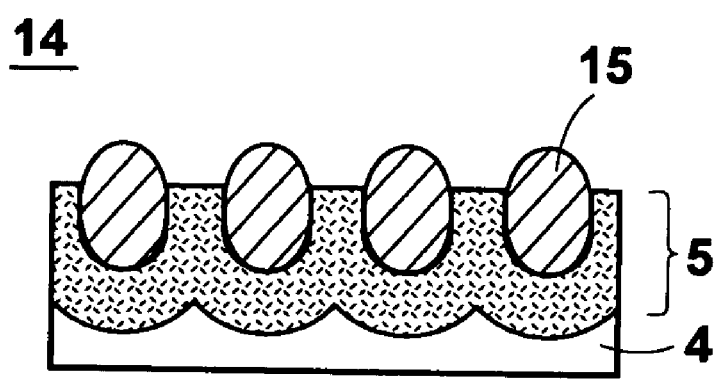
FIG. 4 is a schematic cross-sectional view of a microstructure prepared for comparison.

In order to confirm the effect of the microstructure 3, the present inventor has made an experiment on the microstructure 3 and a microstructure for comparison 14 as illustrated in FIG. 4, which is a schematic cross-sectional view of the microstructure for comparison 14.

The microstructure for comparison 14 illustrated in FIG. 4 is produced as follows.

An alumina layer 5 is formed as a surface layer of an aluminum layer 4 by anodic oxidation of the aluminum layer 4, and minute pores spontaneously formed in the alumina layer 5 are filled with gold by electroplating. However, unlike the microstructure 3 according to the present invention, the electroplating is terminated before gold grows from the minute pores to the portions of the surface of the substrate around the minute pores, and thereafter an upper portion of the alumina layer 5 is removed by chemical polishing so that the head portions of the minute gold particles 15 protrude from the upper surface of the remaining portion of the alumina layer 5. The diameters and depths of and the gaps between the minute pores in the microstructure for comparison 14 are identical to those in the microstructure 3. That is, the sizes and shapes of the base portions of the minute gold particles 15 in the microstructure for comparison 14 are almost identical to the sizes and shapes of the base portions of the minute gold particles 8 in the microstructure 3.

Figure 5:
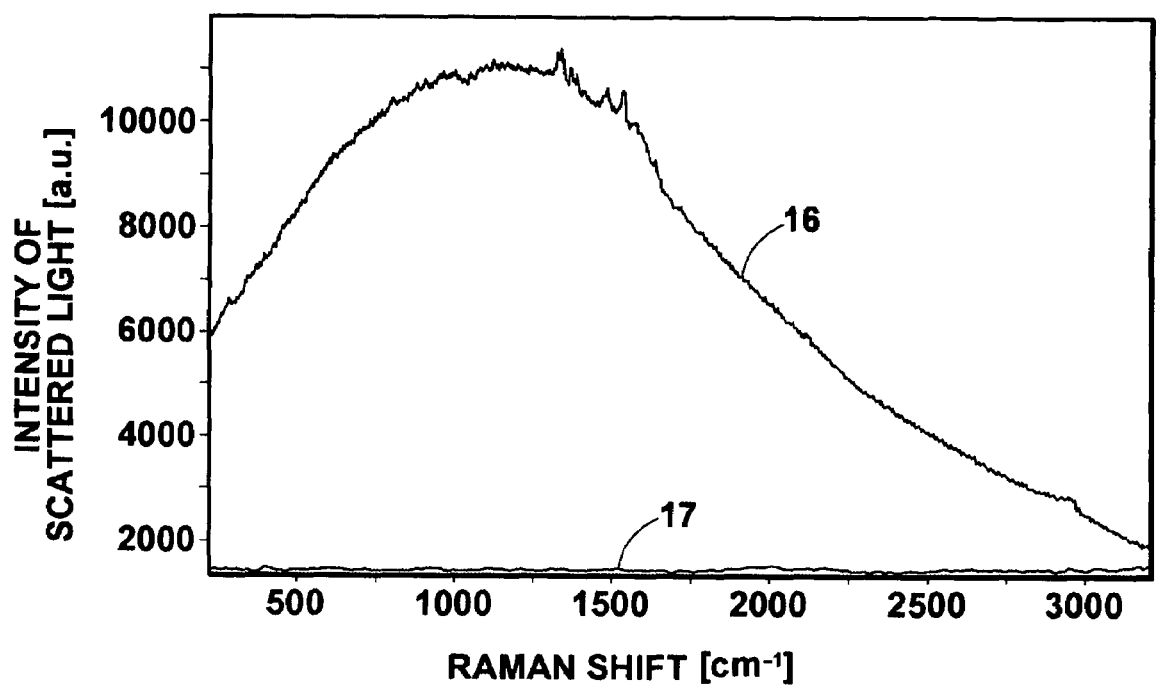
FIG. 5 is a graph indicating examples of Raman spectra.

FIG. 5 is a graph indicating Raman spectra obtained by performing Raman spectrometry using the microstructure 3 and the microstructure for comparison 14, where polymethyl methacrylate (PMMA) is used as a specimen. In FIG. 5, the abscissa corresponds to the Raman shift ($cm^{-1}$), i.e., the reciprocal of the wavelength of light, and the ordinate corresponds to the intensity of the scattered light (indicated by an arbitrary unit (a.u.)).

In FIG. 5, the spectrum 16 is obtained by the Raman spectrometry using the microstructure 3, and the spectrum 17 is obtained by the Raman spectrometry using the microstructure for comparison 14. As clearly indicated in FIG. 5, when an effective Raman spectrum is not obtained by the Raman spectrometry using the microstructure for comparison 14. On the other hand, an effective Raman spectrum is obtained by the Raman spectrometry using the microstructure 3 since the intensity of the Raman scattered light is significantly increased when the microstructure 3 is used.

ADVANTAGES OF THE EMBODIMENT

In the microstructure 3 according to the present embodiment, the minute gold particles 8 having such sizes that the minute gold particles 8 can excite localized plasmon resonance are distributed on the surface of the microstructure 3 with high density. In addition, the gaps between the minute gold particles in the microstructure 3 are smaller than those in the conventional microstructure. Therefore, when the microstructure 3 is used in Raman spectrometry, the Raman scattered light is sufficiently amplified, and the precision of the Raman spectrometry is improved.

Further, since the minute gold particles 8 are arranged in and on minute pores which are formed in advance in a certain arrangement, the entire surface of the microstructure 3 is uniformly arranged. Therefore, the amplification factor at every portion of the surface of the microstructure 3 is approximately identical.

Furthermore, since the arrangement in the microstructure 3 can be controlled by adjustment of the dimensions of the minute pores 6 which are formed on the substrate in advance, it is possible to stably supply microstructures 3 having equal quality in the manufacturing stage. In particular, when the microstructures 3 are manufactured by a combination of anodic oxidation and plating, it is possible to relatively easily control the sizes and shapes of the minute gold particles and the gaps between the minute gold particles, and keep the manufacturing cost of the microstructure 3 low.

When Raman spectrometry is performed by using a Raman spectrometric system comprising the microstructure 3, the increase in the intensity of the Raman scattered light enables detection of the Raman scattered light with high accuracy and achievement of precise Raman spectrometry. Since the Raman spectrometry is widely used in various fields for determination of molecular structures and identification of known and unknown materials, the microstructure, the Raman spectrometric system, and the process for performing Raman spectrometry according to the present invention are highly useful.

Figure 6:
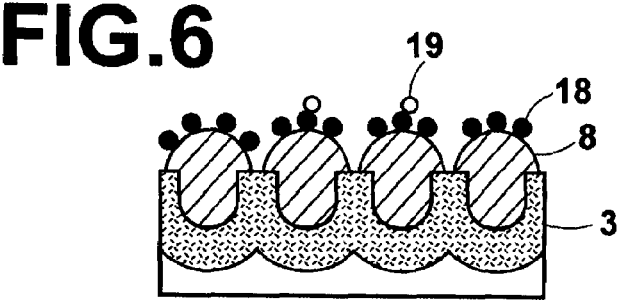
FIG. 6 is a schematic cross-sectional view of a microstructure according to the embodiment, where a predetermined material is fixed to the upper surface of the microstructure.

Modifications and Variations (1) It is possible to fix a material which can be specifically bound to a specimen material to be subject to the Raman spectrometry, to the minute gold particles 8 in the microstructure 3. For example, as illustrated in FIG. 6, when an antigen material 19 is the specimen material, it is possible to fix an antibody material 18 to the minute gold particles 8 in advance so that the antigen material 19 can be specifically bound to the antibody material 18 when the antigen material 19 comes into contact with the antibody material 18. In this case, spectra obtained by the Raman spectrometry using the microstructure 3 to which the antibody material 18 is fixed greatly change when the antigen material 19 is specifically bound to the antibody material 18. It is preferable to determine the material fixed to the minute gold particles 8 differently according to the type of the specimen material. A known combination of the antibody material 18 and the antigen material 19 is a combination of streptavidin and biotin.

(2) Although the diameters of the head portions of the minute gold particles 8 are about 200 nm in the embodiment explained before, the head portions of the minute metal particles can have arbitrary diameters as far as the minute metal particles can excite localized plasmon resonance. Since the localized plasmon resonance (the effect of increasing the intensity of the Raman scattered light) occurs when the diameters of the head portions of the minute metal particles are smaller than the wavelength of the light, it is preferable that the diameters of the head portions of the minute metal particles are about 200 nm or smaller. However, according to the wavelength of the laser light, localized plasmon resonance can be excited even when the diameters of the head portions of the minute metal particles are slightly greater than 200 nm. Therefore, microstructures having such minute metal particles are also included in the scope of the present invention.

(3) Although the gaps between the minute pores 6 are about 300 nm in the embodiment explained above, the gaps between the minute pores 6 are not limited to such a value. In order to make sure that laser light is surely applied to at least one of the minute gold particles, it is preferable that the gaps between the minute pores 6 are equal to or smaller than the beam diameter of the laser light, and are normally about 1 micrometer or smaller.

(4) In order to enhance the effect of increasing the intensity of the Raman scattered light, it is important to reduce the gaps between the head portions of the minute metal particles. Therefore, when the gaps between the minute pores are great, the diameters of the head portions of the minute metal particles are required to be increased in correspondence with the gaps between the minute pores. On the other hand, when the gaps between the minute pores are small, the difference between the diameters of the head portion and the base portion of each of the minute metal particles can be small.

(5) The material with which the minute pores 6 are filled, i.e., the material of which the minute metal particles are made, may be a metal other than gold, and for example, silver, copper, aluminum, nickel, cobalt, or the like. However, since gold is superior in corrosion resistance, and can be evaporated at a relatively low temperature, the minute pores 6 can be easily filled with gold.

(6) The minute pores in the microstructure according to the present invention can be formed by using one of other fine fabrication techniques such as electron beam exposure, nanoimprinting, and near-field light lithography. In this case, the substrate may not be made of aluminum. For example, it is possible to form on a conductive layer a dielectric layer made of a dielectric material such as glass or a resist, and produce minute pores passing through the dielectric layer and extending to the conductive layer by using one of the above fine fabrication techniques.

(7) The microstructure, the process for producing the microstructure, the Raman spectrometric system, and the process for performing Raman spectrometry according to the present invention are not limited to the embodiment and its modifications and variations mentioned above. All suitable modifications and equivalents which will readily occur to those skilled in the art are regarded as falling within the scope of the invention.

All of the contents of the Japanese patent application No. 2003-411790 are incorporated into this specification by reference.

What is claimed is:

1. A microstructure comprising:
   a substrate having a surface at which a plurality of minute pores are formed; and
   a plurality of minute metal particles being arranged at said plurality of minute pores and having such sizes that the plurality of minute metal particles can cause localized plasmon resonance;
   wherein said plurality of minute pores are dispersedly distributed over said surface in such a manner that gaps between adjacent ones of the plurality of minute pores are 1 micrometer or smaller, said plurality of minute metal particles have head portions protruding from said surface, and the head portions have first diameters greater than second diameters which the plurality of minute pores have.

2. A microstructure according to claim 1, wherein gaps between the head portions of adjacent ones of the plurality of minute metal particles are 10 nm or smaller.

3. A microstructure according to claim 1, wherein said substrate has as a surface layer an alumina layer which is formed by anodic oxidation of a material containing aluminum as a main component, and said plurality of minute pores are formed during the anodic oxidation.

4. A microstructure according to claim 1, wherein said first diameters are 200 nm or smaller.

5. A microstructure according to claim 1, wherein said plurality of minute pores have depths of 100 nm or smaller.

6. A microstructure according to claim 1, wherein said second diameters have a variance of 15% or smaller.

7. A microstructure according to claim 1, wherein said plurality of minute metal particles are made of one of gold, silver, aluminum, and copper.

8. A process for producing a microstructure in which a plurality of minute metal particles having such sizes that the plurality of minute metal particles can cause localized plasmon resonance are dispersedly distributed over a surface, said process comprising the steps of:
   (a) forming a plurality of minute pores in a surface layer of a substrate in such a manner that the plurality of minute pores are dispersedly distributed, and gaps between adjacent ones of the plurality of minute pores are 1 micrometer or smaller;
   (b) filling said plurality of minute pores with metal by plating so as to form base portions of said plurality of minute metal particles; and
   (c) continuing said plating until head portions are formed on the base portions of said plurality of minute metal particles, where the head portions protrude from said surface layer and have first diameters greater than second diameters which the plurality of minute pores have.

9. A process according to claim 8, wherein said substrate is made of a material containing aluminum as a main component, and said plurality of minute pores are formed in said surface layer by anodic oxidation of said substrate.

10. A process according to claim 8, wherein said plating is continued until gaps between the head portions of adjacent ones of the plurality of minute metal particles become 10 nm or smaller.

11. A process for performing Raman spectrometry, comprising the steps of:
   (a) making a specimen material absorbed by a first surface of a microstructure;
   (b) applying light to said first surface of the microstructure; and
   (c) obtaining a spectrum of scattered light generated by scattering of said light at said first surface of the microstructure;
   wherein said microstructure includes,
      a substrate having a second surface at which a plurality of minute pores are formed, and
      a plurality of minute metal particles being arranged at said plurality of minute pores and having such sizes that the plurality of minute metal particles can cause localized plasmon resonance;
   said plurality of minute pores are dispersedly distributed over said second surface in such a manner that gaps between adjacent ones of the plurality of minute pores are 1 micrometer or smaller, said plurality of minute metal particles have head portions protruding from said second surface, and the head portions have first diameters greater than second diameters which the plurality of minute pores have; and
   said head portions and said second surface constitute said first surface.

12. A process according to claim 11, wherein gaps between the head portions of adjacent ones of the plurality of minute metal particles are 10 nm or smaller.

13. A Raman spectrometric system comprising:
   a microstructure having a first surface;
   a light application unit which applies light to said first surface of the microstructure; and
   a spectroscopic unit which obtains a spectrum of scattered light generated by scattering of said light at said first surface of the microstructure;
   wherein said microstructure includes,
      a substrate having a second surface at which a plurality of minute pores are formed, and
      a plurality of minute metal particles being arranged at said plurality of minute pores and having such sizes that the plurality of minute metal particles can cause localized plasmon resonance;
   said plurality of minute pores are dispersedly distributed over said second surface in such a manner that gaps between adjacent ones of the plurality of minute pores are 1 micrometer or smaller, said plurality of minute metal particles have head portions protruding from said second surface, and the head portions have first diameters greater than second diameters which the plurality of minute pores have; and
   said head portions and said second surface constitute said first surface.

14. A Raman spectrometric system according to claim 13, wherein gaps between the head portions of adjacent ones of the plurality of minute metal particles are 10 nm or smaller.

* * * * *